(12) United States Patent
Schieve

(10) Patent No.: US 12,059,548 B2
(45) Date of Patent: Aug. 13, 2024

(54) SELF-COMPENSATING CHUCKING DEVICE FOR INFUSION PUMP SYSTEMS

(71) Applicant: CareFusion 303, Inc., San Diego, CA (US)

(72) Inventor: Eric W. Schieve, Del Mar, CA (US)

(73) Assignee: CareFusion 303, Inc., San Diego, CA (US)

(*) Notice: Subject to any disclaimer, the term of this patent is extended or adjusted under 35 U.S.C. 154(b) by 227 days.

(21) Appl. No.: 17/351,039

(22) Filed: Jun. 17, 2021

(65) Prior Publication Data

US 2021/0308365 A1    Oct. 7, 2021

Related U.S. Application Data

(63) Continuation of application No. 14/968,741, filed on Dec. 14, 2015, now Pat. No. 11,045,599.

(51) Int. Cl.
*A61M 5/142* (2006.01)
*A61M 5/158* (2006.01)

(52) U.S. Cl.
CPC ........ *A61M 5/142* (2013.01); *A61M 5/14228* (2013.01); *A61M 5/14244* (2013.01); *A61M 2005/14264* (2013.01); *A61M 5/158* (2013.01)

(58) Field of Classification Search
CPC .............. A61M 5/142; A61M 5/14228; A61M 5/14244; A61M 5/158;

(Continued)

(56) References Cited

U.S. PATENT DOCUMENTS 1,478,706 A * 12/1923 Forker .................. E05D 3/02
                                                        16/381
4,689,043 A    8/1987 Bisha
(Continued)

FOREIGN PATENT DOCUMENTS

DE    8914784 U1    2/1990
EP    2621255 A2    7/2013
(Continued)

OTHER PUBLICATIONS

International Search Report and Written Opinion for Application No. PCT/US2016/066213, dated May 23, 2017, 14 pages.

*Primary Examiner* — Kami A Bosworth
*Assistant Examiner* — Avery Smale
(74) *Attorney, Agent, or Firm* — Morgan, Lewis & Bockius LLP

(57) ABSTRACT

A self-compensating chucking device may be provided. The chucking device may form a portion of a latching door handle of a door of an infusion pump. The door and a housing of the infusion pump may form a clam-shell clamp that secures infusion tubing to pumping mechanisms of the infusion pump. The latching door handle may include a latching door mechanism that includes a tapered pin. The tapered pin may extend through an outer portion of a door housing, an opening in a handle of the door, and into an opening in an inner portion of the door housing. The opening in the handle of the door may have a tapered inner surface that corresponds to the taper the tapered pin to form the chucking device. The pin may include a groove configured to accept an E-clip that retains the tapered pin within the door housing.

20 Claims, 11 Drawing Sheets

(58) Field of Classification Search
CPC ........ A61M 2005/14264; A61M 25/02; A61M 60/81; A61M 1/152; Y10T 292/0911; Y10T 292/0948; Y10T 292/0949; Y10T 292/0894; E05D 3/02; E05D 2005/106; F16B 4/004; F04B 43/08; F04B 43/12; F04B 45/06; F04B 45/08; F04B 39/12; F04B 39/121; F04B 53/16; F04B 39/14; F04B 53/22

See application file for complete search history.

(56) References Cited

U.S. PATENT DOCUMENTS

| | | | |
|---|---|---|---|
| 5,237,723 A | 8/1993 | Little | |
| 5,482,446 A * | 1/1996 | Williamson | F04B 43/082 |
| | | | 417/474 |
| 5,807,333 A * | 9/1998 | Osborne | A61M 5/14232 |
| | | | 604/151 |
| 2009/0275897 A1 | 11/2009 | Kasai et al. | |
| 2012/0156073 A1* | 6/2012 | Haylor | A61M 5/14228 |
| | | | 417/474 |
| 2013/0138074 A1 | 5/2013 | Travis et al. | |
| 2014/0100526 A1 | 4/2014 | Ueda | |

FOREIGN PATENT DOCUMENTS

| | | |
|---|---|---|
| GB | 303640 A | 1/1929 |
| WO | WO-9856453 A1 | 12/1998 |

\* cited by examiner

SELF-COMPENSATING CHUCKING DEVICE FOR INFUSION PUMP SYSTEMS

CROSS-REFERENCE TO RELATED APPLICATIONS

The present application is a continuation of U.S. patent application Ser. No. 14/968,741, filed on Dec. 14, 2015, the entirety of which is incorporated herein by reference.

BACKGROUND

Technical Field

The present disclosure generally relates to the administration of medical fluid by infusion and, in particular, relates to systems and methods of securing infusion tubing to an infusion pump for providing and pumping medical fluid.

Background

Infusion pumps have become commonplace within the healthcare industry as a devices for precisely administering intravenous (IV) fluids. Use of a pump in place of an elevated fluid container with a simple roller clamp to control the flow of the IV fluid allows more accurate and consistent control of the rate of delivery of the fluid to the patient.

The assembly of tubing, valves, fittings, and needles that connect the fluid container to the patient may be referred to as an "IV set." IV sets are typically disposable to reduce the risk of infection and contamination. When used with an infusion pump, the IV set includes a segment intended to be manipulated by the pump to cause the fluid to flow at a controlled rate. For a peristaltic type of pump, this may be as simple as a length of tubing that is captured between two halves of a clam-shell style pumping mechanism to fit the tubing into a pumping compartment.

SUMMARY

An improved latching door mechanism is provided. The improved latching door mechanism may be provided for a clam-shell door for capturing IV tubing in an intravenous infusion pump system for secure, reliable, positioning of the tubing over many uses of the pump system. The latching door mechanism may include a latch having a self-adjusting chucking mechanism that helps ensure secure, reliable latching of the door over the lifetime of the pump. The latching door mechanism may include a tapered pin configured to support, mechanically retain, and allow rotational pivoting of a latching door handle, by interaction with a complimentary tapered hole mating interface.

Certain exemplary embodiments of the present disclosure include an infusion pump, including: a housing; at least one pumping mechanism; and a pivoting door configured to close and latch to secure infusion tubing to the at least one pumping mechanism, wherein the pivoting door includes: a handle having recess and an opening in the recess; a door housing having an inner portion and an outer portion; and a tapered pin that extends through an opening in the outer portion, a co-aligned opening in the recess of the handle, and a co-aligned opening in the inner portion.

In another embodiment, a latching door handle assembly for a door of an infusion pump is disclosed that includes a molded handle having a hook portion with a recess and a tapered opening in the recess; and a tapered pin, wherein the tapered pin includes: a tapered portion configured to engage in the tapered opening; and a groove configured to receive an E-clip disposed in the recess.

In another embodiment, a fluid infusion system is provided that includes: an intravenous (IV) set having IV tubing; and an IV pump having a pumping module and a door, wherein a pumping segment of the IV tubing is secured to the pumping module by the door, and wherein the door includes: a door housing having an outer portion, an inner portion, and an air gap between the outer portion and the inner portion; a handle having a tapered opening disposed in the air gap; and a latching door handle assembly that includes a tapered pin that extends through an opening in the outer portion, through the tapered opening in the air gap, and into a co-aligned opening in the inner portion.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

While the following discussion is directed to the administration of medical fluid to a patient by a nurse using an IV pump, the disclosed methods and configurations may be used for other medical and non-medical applications and may be used by other individuals, for example a patient self-administering a medical fluid at home.

Figure 1:
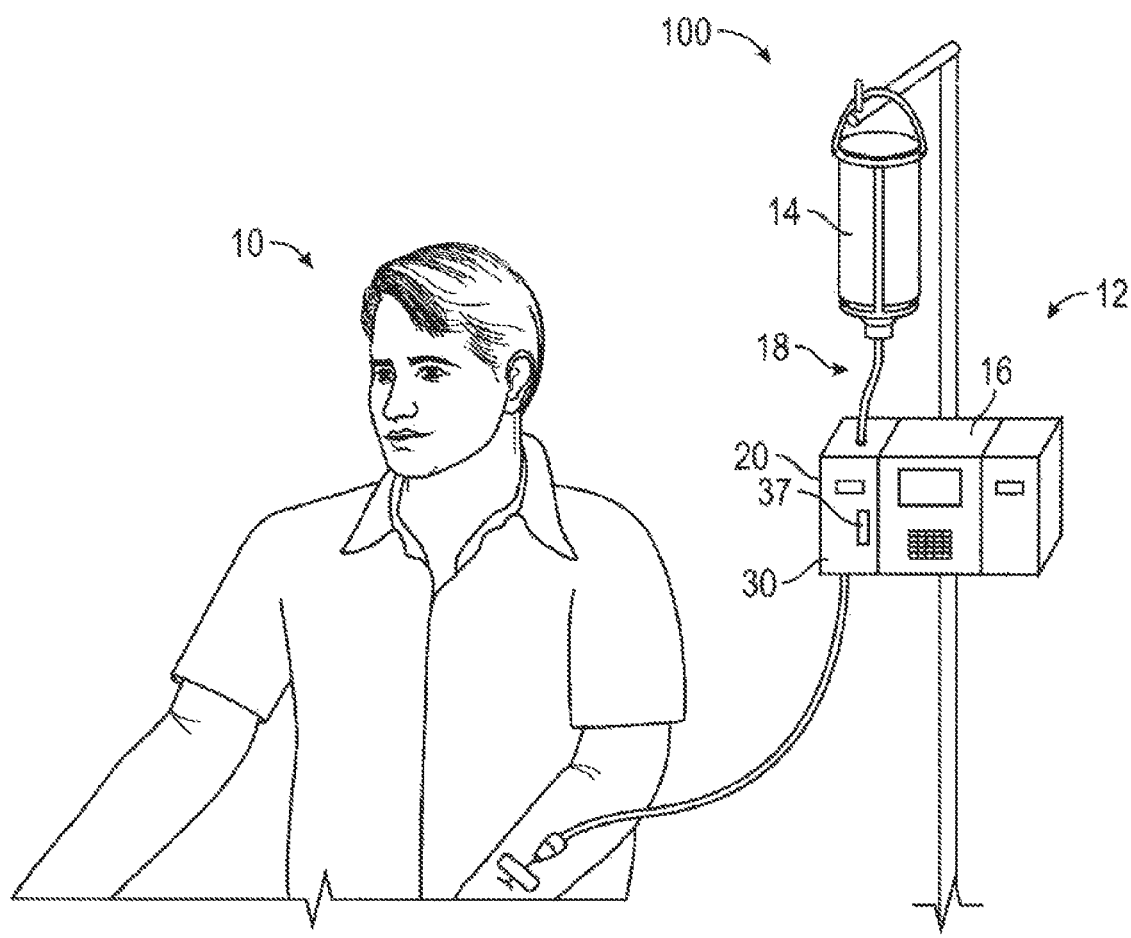
FIG. 1 is a diagram of a system for administering medical fluid to a patient using an IV pump according to certain aspects of the present disclosure.

FIG. 1 is a diagram of a system 100 for administering medical fluid to a patient 10 using an IV pump 12. As shown in FIG. 1, a fluid container 14 may be hung at or above the patient's head and connected via an IV set 18 to an IV pump 12 and then to the patient 10. In this example, the IV pump 12 includes a control module 16 and a pumping module 20. A portion of IV set 18 may be secured to pumping module 20 by a door 30. Door 30 may be a pivoting door that is rotatable about hinge portions 60 and may be provided with a latching mechanism 37 operable to securely fasten door 30 in a closed position to secure the portion of the IV set in position for pumping. Latching mechanism 37 may also be operable to release door 30 so that door 30 can pivot to an open position to release IV set 18.

Figure 2:
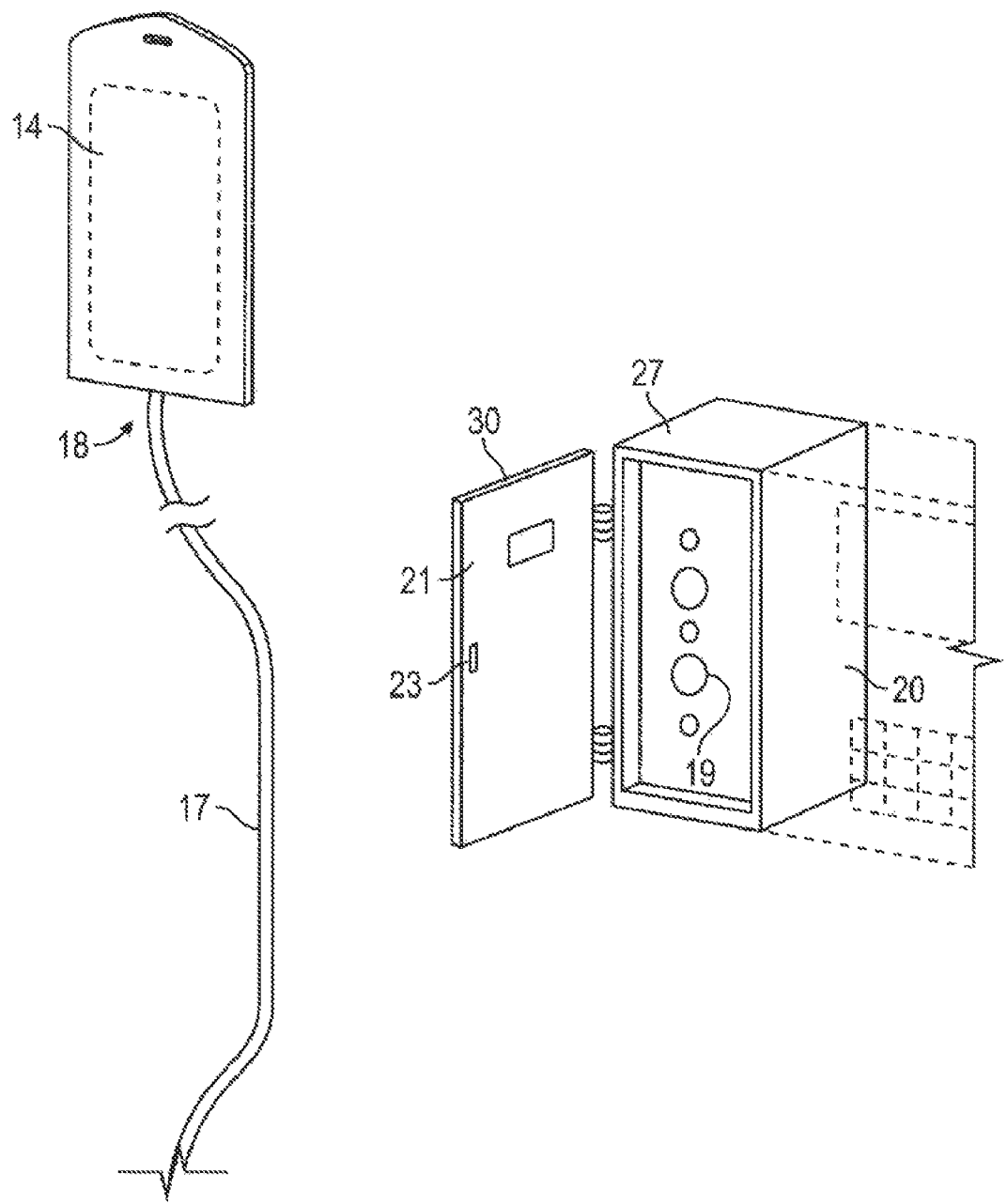
FIG. 2 illustrates a pumping segment of an IV set fitting into the pump module of the IV pump of FIG. 1 according to certain aspects of the present disclosure.

FIG. 2 illustrates a pumping segment 17 of IV set 18 that may be secured into the pump module 20 of the IV pump 12 of FIG. 1. In this example, pumping element 17 is a length of the tubing of IV set 18. The pumping module 20 is shown with its front door 30 opened and the inner surface 21 of door 30 and the pumping actuators 19 of pump module 20 visible. When installed, the pumping element 17 is located against the pumping actuators 19 and door 30 can be closed and latched using an internal member 23 of latch 37 to secure pumping element 17 against pumping actuators 19. Pumping actuators 19 may be operated to sequentially compress portions of pumping element 17 to apply force to the fluid and sequentially advance fluid toward the patient 10 at a controlled flow rate.

An exemplary implementation of infusion pump 12 is shown in FIGS. 3A, 3B, 4A and 4B. As shown in FIGS. 3A, 3B, 4A and 4B, an infusion pump of a fluid infusion system may include a housing 27 which accommodates one or more pumping mechanisms (e.g., a cam mechanism that controls a plurality of fingers of a peristaltic pumping mechanism, an electric motor and associated gearing that drive said cam mechanism) and further accommodates electronic control and processing circuitry for controlling the pumping mechanisms and processing signals (e.g., from pressure sensors, etc.) provided on the unit.

Figure 4A:
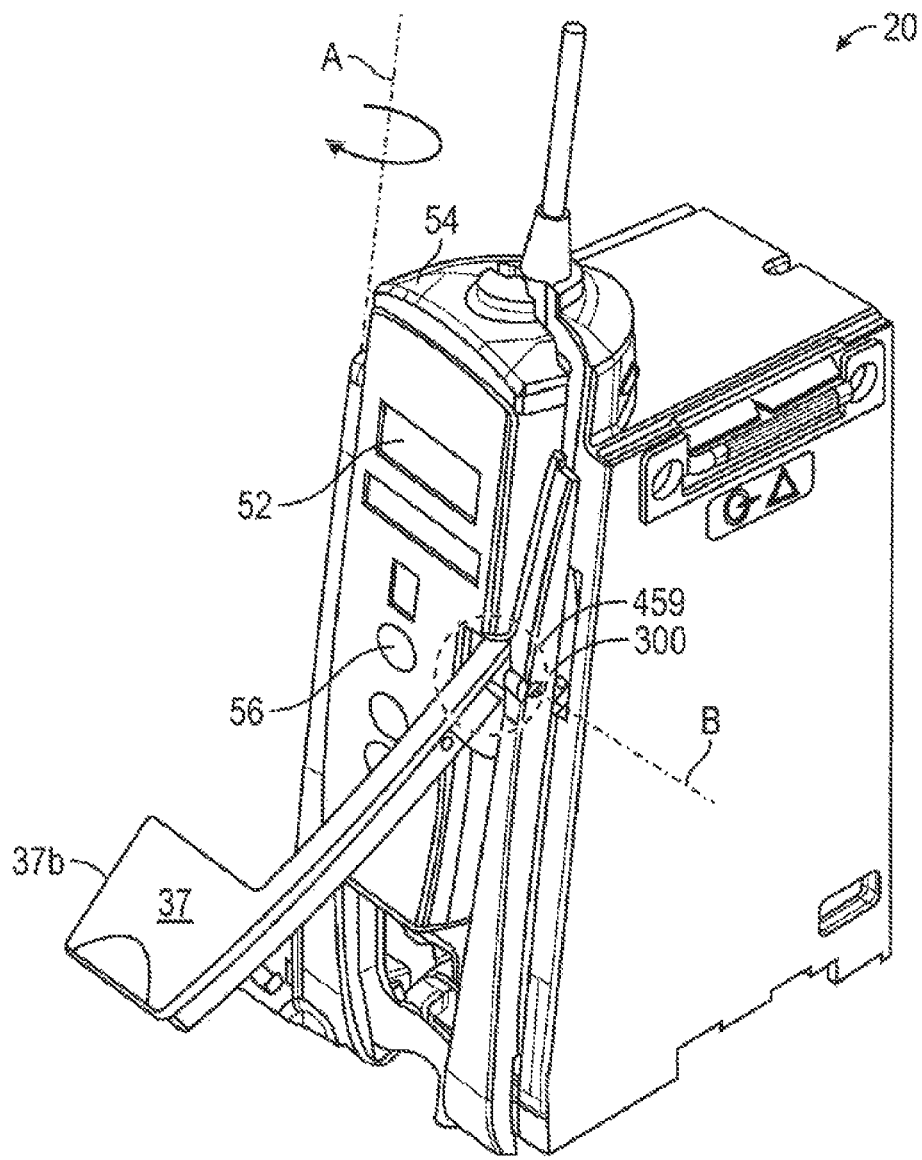
FIG. 4A is a perspective view of the infusion pump of FIG. 3A, with the door in a closed and unlatched position according to certain aspects of the present disclosure.
Figure 4B:
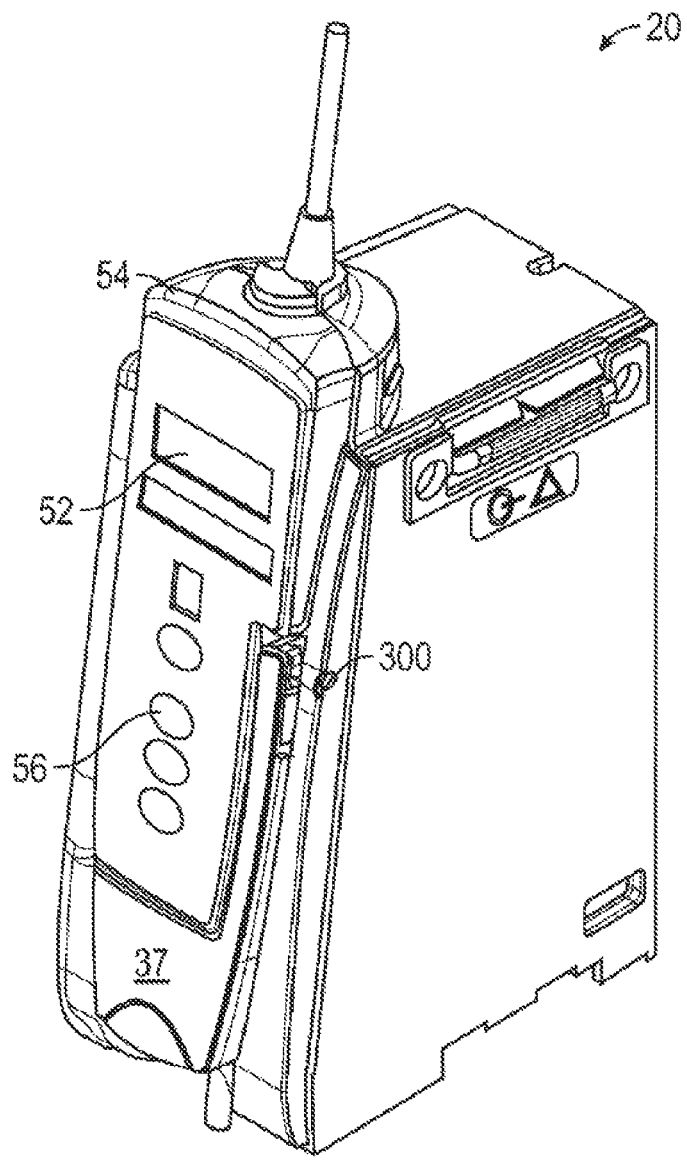
FIG. 4B is a perspective view of the infusion pump of FIG. 3A, with the door in a closed and latched position according to certain aspects of the present disclosure.

The pump unit 12, as shown in FIGS. 4A and 4B, may also include an electronically operated display 52, an alarm light 54, an input keyboard 56 or other manually operated controls. The rear of the unit 12 (not shown) may be provided with various connectors including connectors for receiving complementary power supply connectors, electronic communications interfacing connectors for providing data and alarm output signals and for receiving input signals, and/or mechanical supports.

Figure 3A:
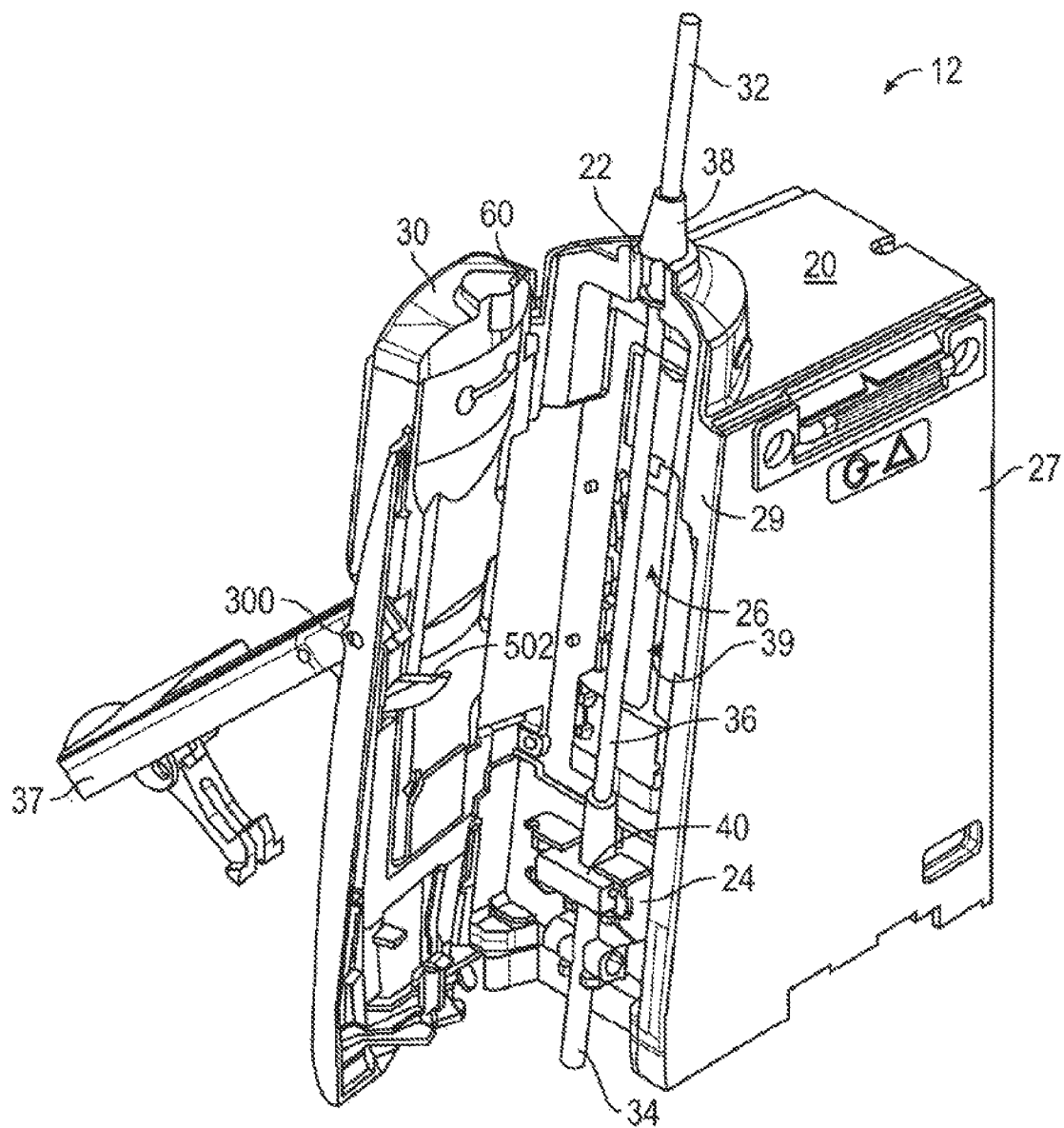
FIG. 3A illustrates a perspective view of an infusion pump with a door in an open position and showing part of a pumping segment of an IV set fitting into the pump module of the infusion pump according to certain aspects of the present disclosure.

In the example of FIG. 3A, the front of the housing 27 includes a face or deck 29 on which is exposed an upper mounting or bracket 22 for a complementary fitting 38 forming part of an infusion line; a lower mounting or bracket 24 for a complementary fitting 40 forming part of such infusion line and a peristaltic assembly 26 which is, effectively, the operative end of the peristaltic pumping mechanism and may, in principle, be the free ends of respective fingers moveable, by the cam mechanism referred to, inwards and outwards from the face or deck 29.

In order to make it easier to maintain sterile conditions, these fingers may be covered by a thin flexible membrane (not shown) sealed at its edges with respect to the deck 29. Door 30 is may be fitted to the housing 27 and can be swung between an open position illustrated in FIGS. 3A and 3B and a closed position illustrated in FIGS. 4A and 4B, about a pivotal axis A.

A medical fluid infusion line, for use with the pump unit, may include upper and lower sections 32 and 34 respectively of transparent (e.g., plastic) tubing, an intermediate section 36 of resiliently compressible tubing, (e.g., formed from silicone rubber), and upper and lower fittings 38 and 40 via which the tubing section 36 is connected respectively with the upper line 32 and with the lower line 34. In use, the upper line 32 may extend upwardly to a source 14 of the medical fluid to be administered and the lower line 34 may extend from the infusion pump to an infusion needle or catheter or the like inserted into the patient 10. In use, the infusion line may be extended across the face or deck 29 of the pump unit so that the fittings 38 and 40 are received in the brackets 22 and 24 respectively and so that the tubing section 36 extends over the peristaltic assembly 26 as illustrated in FIGS. 3A and 3B.

Figure 3B:
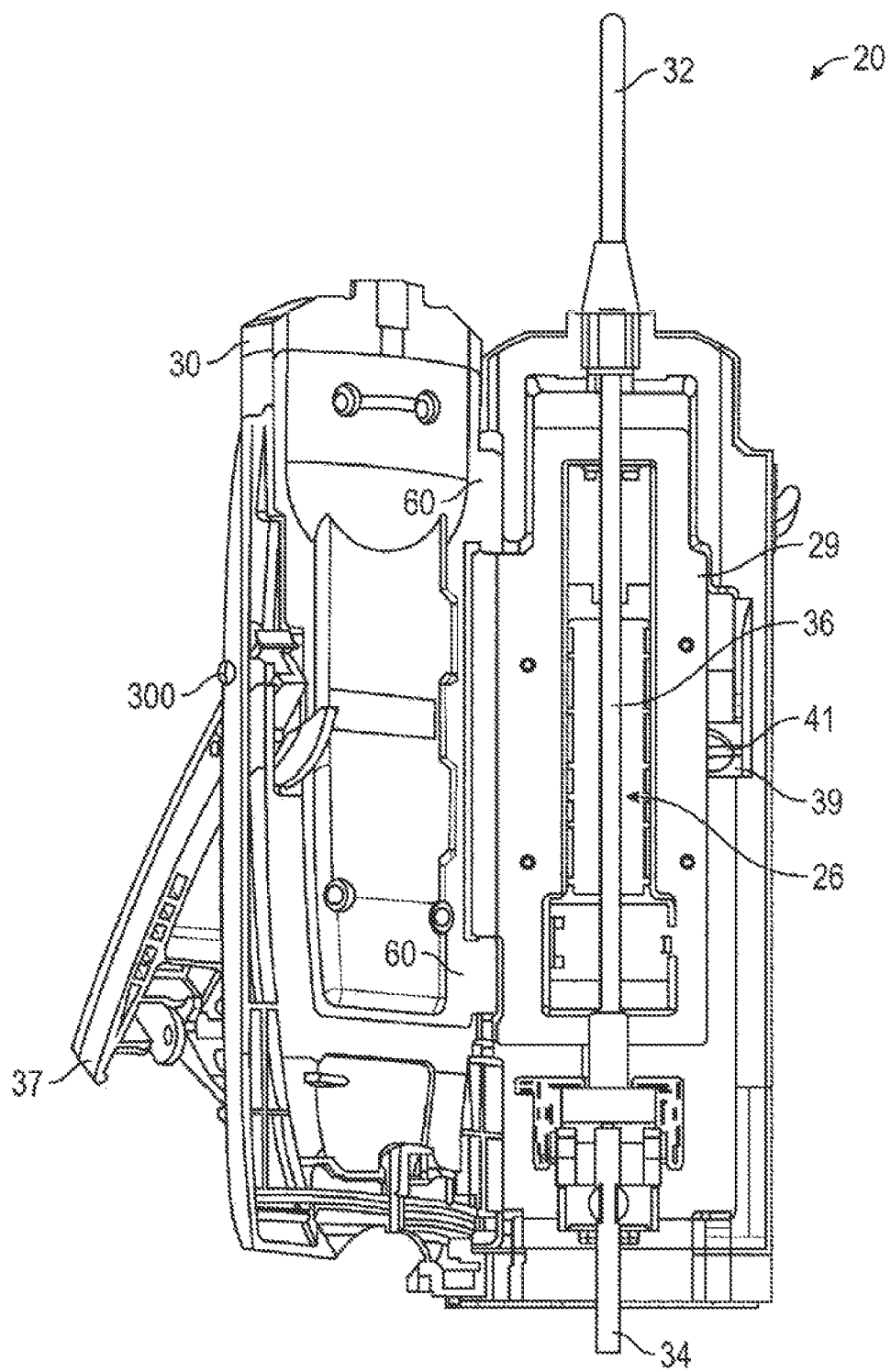
FIG. 3B illustrates a front view of the infusion pump of FIG. 3A according to certain aspects of the present disclosure.

The infusion line may be fitted in place in this fashion while door 30 is in the open position shown in FIGS. 3A and 3B. After the infusion line has been so fitted, door 30 may be moved to the closed position shown in FIG. 4A and secured using catch 37 which comprises a lever mounted on the outer edge of the door 30 (e.g., the edge which lies at the side of the pump unit when the door is in its closed position), by a pin 300 for pivoting about an axis B (see, e.g., FIG. 4A) that is generally perpendicular to that outer edge of the door and parallel with the front face of the door.

As shown in FIG. 4A, catch 37 may have a handle portion 37b which extends downwardly and into a pocket in the front of the door 30. Catch 37 may also include a cam portion (described in further detail hereinafter) adapted to fit within a complementary recess 39, in deck 29 and obscured by the outer housing 27, at the front right of the pump housing adjacent side of the pump.

The cam portion of the catch 37 may have a cam surface 502, (see FIG. 5), configured to engage under an internal yoke boss 41 or other corresponding cam feature (which projects laterally from the pump housing into recess 39) when, with the pump door 30 closed, the handle portion 37b is swung downwardly and rearwardly from a position in which it projects forwards and outwards from the door (FIG. 4A) to a position in which the handle portion 37b lies against the front of the door (FIG. 4B).

In operation of the pump, the fingers of the peristaltic assembly 26 periodically press the flexible resilient tubing against a counter surface or anvil to propel fluid within the infusion line along the latter. In one exemplary implementation of the pump, the peristaltic assembly comprises an upper finger and a lower finger, which are of a relatively limited extent in the longitudinal direction of the infusion line, and an intermediate finger or pad, between the upper and lower fingers, in which the intermediate finger is extended or elongated in the longitudinal direction of the infusion line.

In operation, assuming the fluid is to be propelled downwards, as viewed in FIGS. 1 to 4B, along the infusion line, the peristaltic assembly performs a repeating cycle in which, with the intermediate pad spaced from the counter surface, the upper finger presses the flexible tube against the counter surface or anvil to close the tube at the location of the upper finger, the lower finger is then withdrawn from the counter surface to open the tube at the location of the lower finger. Then the intermediate pad or finger is then moved towards the counter surface to drive the fluid in the tube adjacent the intermediate pad downward along the tube, and then the tube is pinched closed again between the lower finger and the counter surface. The upper finger is then withdrawn from the counter surface and the intermediate finger withdrawn from the counter surface to draw fresh fluid into the part of the tube adjacent the intermediate finger. It should be appreciated that the pumping mechanisms described above in connection with FIGS. 3A-4B are merely illustrative. Other pumping arrangements or mechanisms can be used to pump fluid through infusion tubing (or any other portion of an IV set such as an infusion cassette) that is secured to the pumping mechanisms by a pivoting clam-shell door that is controllable and latchable using a latch mechanism as described herein.

Figure 5:
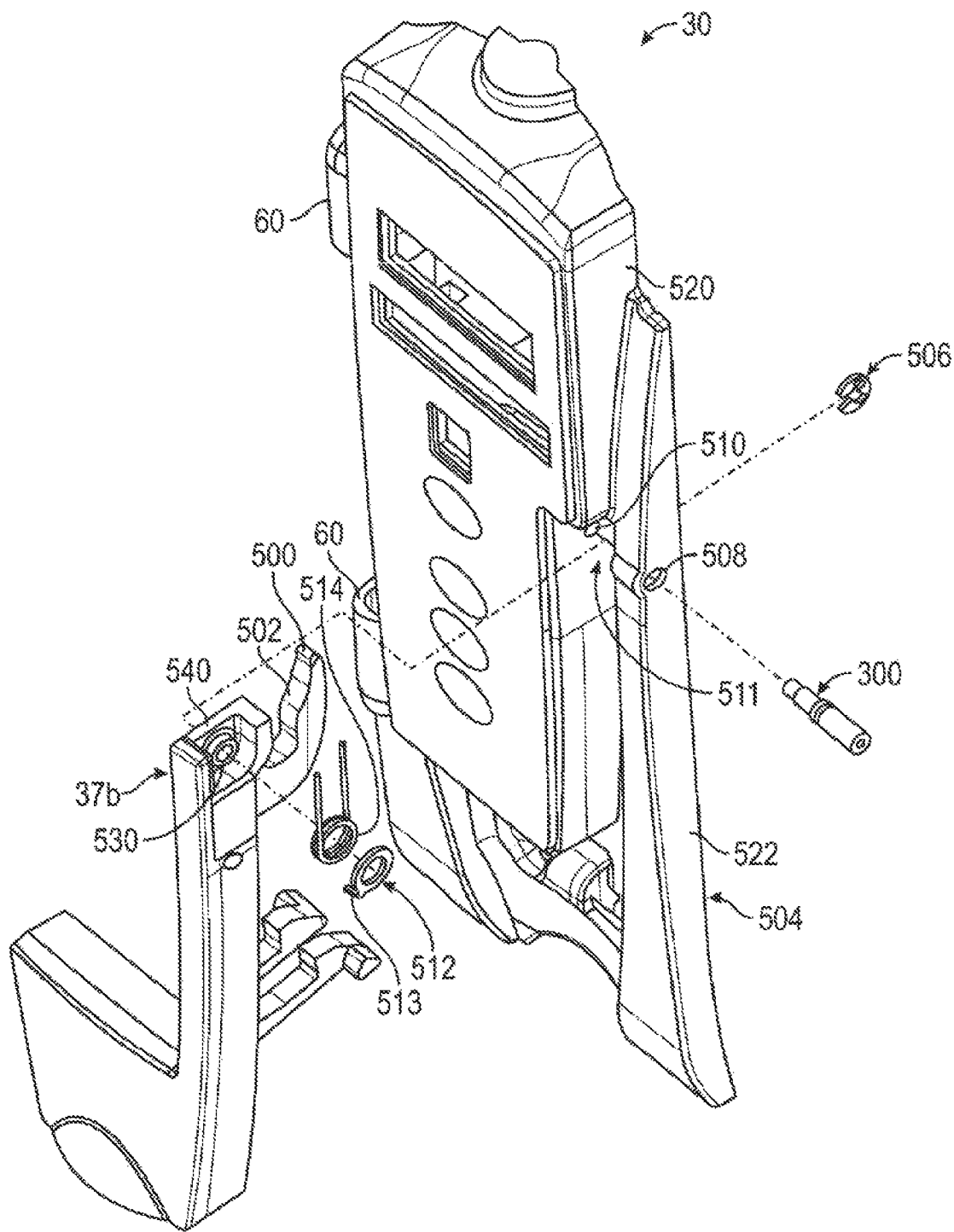
FIG. 5 illustrates an exploded perspective view of a door and latch assembly for an infusion pump according to certain aspects of the present disclosure.

FIG. 5 shows an example of a door assembly 30 having an improved latching door mechanism with a tapered pin 300 designed to support, mechanically retain and allow rotational pivoting of a latching door handle 37b, with a complimentary tapered hole mating interface 530 in the door handle. Tapered pin 300 may be formed from a hardened steel in one embodiment (e.g., an AISI Type 303 Stainless Steel).

An intravenous infusion pump may operate by capturing a fluid delivery tube between two halves of a clam-shell-style pumping mechanism. One half of this clam-shell pump configuration may be a base assembly that houses the primary electro-mechanical pump elements, hinge mounting points to support a door assembly, features that capture and locate the fluid delivery tube and a yoke catch that engages a latching door handle for snug door closure.

Door assembly 30 of FIG. 5 may be coupled to housing 27 of an infusion pump at hinge points 60 to form the second half of a clam-shell pump configuration that mounts to, and rotates about, the hinge mounting points of the other half of the clam shell formed by the housing 27. Door assembly 30 may include, on a rear side (not shown) complimentary features to the pump features of the housing that capture and locate the fluid delivery tube along the mechanical pump elements. Door assembly 30 may include a rotationally pivoted latching door handle 37b that mates with the yoke clamp of the housing, thus allowing this snug door closure.

Tapered pin 300, when installed in the door latch assembly may span an air gap 511 of a rectangular shaped aperture in the door assembly's housing 504 at which the latching door handle 37b is located and supported. The air gap 511 may be disposed between an inner portion 520 and an outer portion 522 of door housing 504. During assembly, the tapered pin 300 may be inserted through a series of mating holes in the following order: a through-hole 508 in outer portion 522, a matching, co-aligned tapered hole 530 in the hook portion 500 of the latching door handle 37b, and a co-aligned blind hole 510 in the inner portion 520 of door housing 504.

Door handle 37b may be a sintered steel handle such as a molded sintered stainless steel handle with a molded hook 500 and a recess 540. Opening 530 may be disposed in recess 540 and may have a tapered inner surface that corresponds to the shape of a tapered outer surface of tapered pin 300. The tapered inner surface of opening 530 may have an approximately 2 degree taper moving inward in a direction from outer portion 522 toward inner portion 520 of housing 504, when door assembly 30 is assembled. A taper interface (e.g., a 2.0 degree taper interface) may be formed from the inclined contact surface made between the tapered pivot latch pin 300 and the interior surface of opening 530 of hook portion 500. Side torque applied to the door handle 37b during closing generates a chucking force along this inclined tapered surface temporarily binding the pivot latch pin and hook together. Simultaneous downward rotation during this "chucking" enables the door handle to properly engage the pump housing thus enabling door closure.

Door housing 504 may be formed from plastic and may include co-aligned openings 508 and 510, respectively, in outer portion 522 and inner portion 520. An inner wall of outer portion 522 and an outer wall of inner portion 520 may form opposing surfaces of the aperture 511 within which pin 300 engages hole 530 of handle 37b.

As shown, a wear protection washer such as washer 512 and the coil of a torsion spring such as spring 514 may be disposed in recess 540 when door assembly 30 is assembled. In the example of FIG. 5, washer 512 includes a retention tab 513 that keys the washer into a gap between recess 540 (e.g., a latch handle spring pocket) and spring 514. However, this is merely illustrative. In some embodiments, washer 512 may be implemented as a flat washer. According to an embodiment, torsion spring 514 extends around the tapered opening in recess 540, washer 512 is disposed on the tapered pin, and E-clip retainer 506 disposed in the e-clip groove 602 between torsion spring 514 and the wear protection washer 512.

Figure 6:
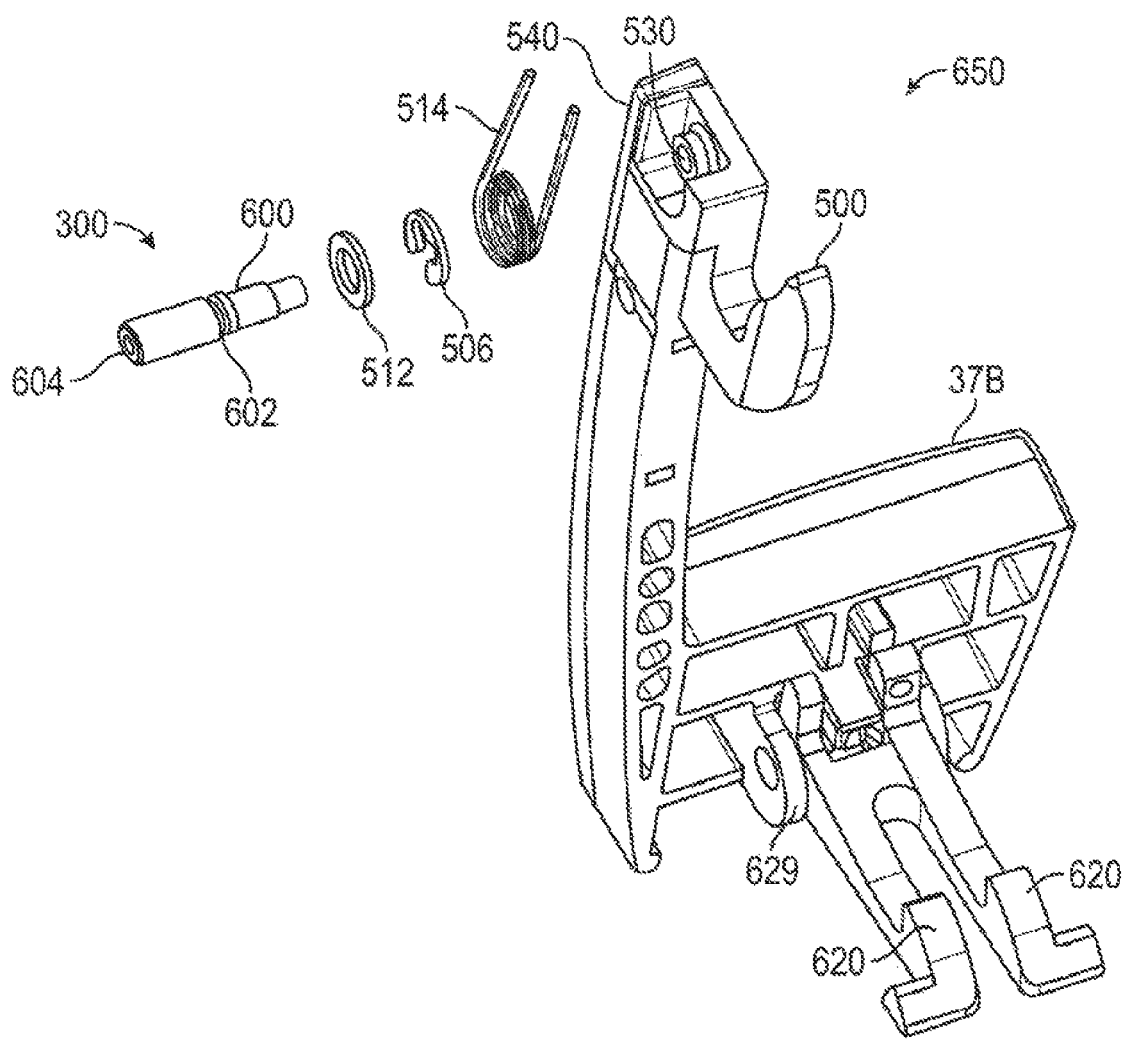
FIG. 6 illustrates an exploded perspective view of a latching door handle assembly according to certain aspects of the present disclosure.

As shown in the exploded perspective view of latching door handle assembly 650 of FIG. 6, features along the body of tapered pin 300 may be provided to securely retain and establish the rotational datum of the latching door handle 37b within the door housing 504. These tapered pin features include the tapered profile geometry of a tapered portion 600 of the pin 300 and an E-clip groove 602.

Tapered section 600 of pin 300 may be configured to mate with a matching tapered inner surface of opening 530 in the hook portion 500 of the latching door handle 37b. As a turning force is applied to the handle 37b, in the un-latched position, to close the door, these two tapered mating features are pushed together (e.g., by a lateral force generated along the tapered interface by turning the handle as the door latch cam surface 502 of handle 37b and a corresponding cam feature in the pump housing are moved into alignment preceding the downward handle cam latching upon a housing catch such as a yoke boss) thereby generating a binding axial friction between pin 300 and the inner surface of opening 530 that binds the pin 300 and handle 37b together along this tapered interface.

During closure, as the door is turned, engagement with the internal components of the pump that capture the tube set resist this door closure, prompting an increase in side turning force to allow alignment of the cam latching elements. Turning force on the door handle 37b, to overcoming the resistance of the internal components of the pump, generates the binding axial friction along the tapered interface 600 and the matching tapered inner surface of opening 530 that temporarily locks the pin 300 and latch door handle 37b together creating a stable rotational pivot axis. This stable pivot axis enables smooth aligned motion between hook 500 of latching door handle 37b and the yoke catch (e.g., a boss) of the housing when the handle is pushed (e.g., downward) to close and latch the door 30.

E-clip groove 602 may be a recess having a complementary shape for accepting E-Clip retainer 506. E-clip retainer 506, when engaged in groove 602 in pin 300, provides a mechanical stop that prevents tapered pin 300 from backing out of door housing 504 during normal operation. When door assembly 30 is assembled, E-clip 506 is located along the tapered pin 300 near the inner surface of the outer portion 522 of the door housing aperture 511. A washer 512 may be placed between E-Clip 506 and the inner surface of outer portion 522 to provide a smooth surface that protects E-clip 506 from damage caused by chaffing against the door housing inner wall. E-clip retainer 506 may, for example, be a Rotoclip® retainer in some embodiments.

For ease of removal from door housing 504 during maintenance and repair operations, a threaded extraction hole 604 may be provided at the exposed end of tapered pin 300. A threaded rod or tool can be inserted into this hole 604 and used to pull pin 300 out of the door housing 504. The extraction hole 604 may be provided with an internal thread (e.g., a #2-56 UNC-2B internal thread). In this way, the extraction hole 604 allows one to pull symmetrically along the tapered pin's axis, enabling easy extraction of the pin during repair or maintenance operations. E-Clip retainer 506 may be removed before engaging the hole 604 to remove the pin 300.

As shown in FIG. 6, handle 37b may include one or more latching extensions such as latching extensions 620. Latching extensions 620 may extend into or below a portion of housing 27 and engage with corresponding mating features of the tube set as part of the infusion tube set functionality in accordance with the pumping mechanisms of pump 12.

Pin 300 may be provided with e-clip recess 602 and without any additional recess as in the example of FIG. 6. Latching extensions 620 are shown in FIG. 6 along with mating features 629 for latching extensions 620 on an interior side of handle 37b.

Figure 7:
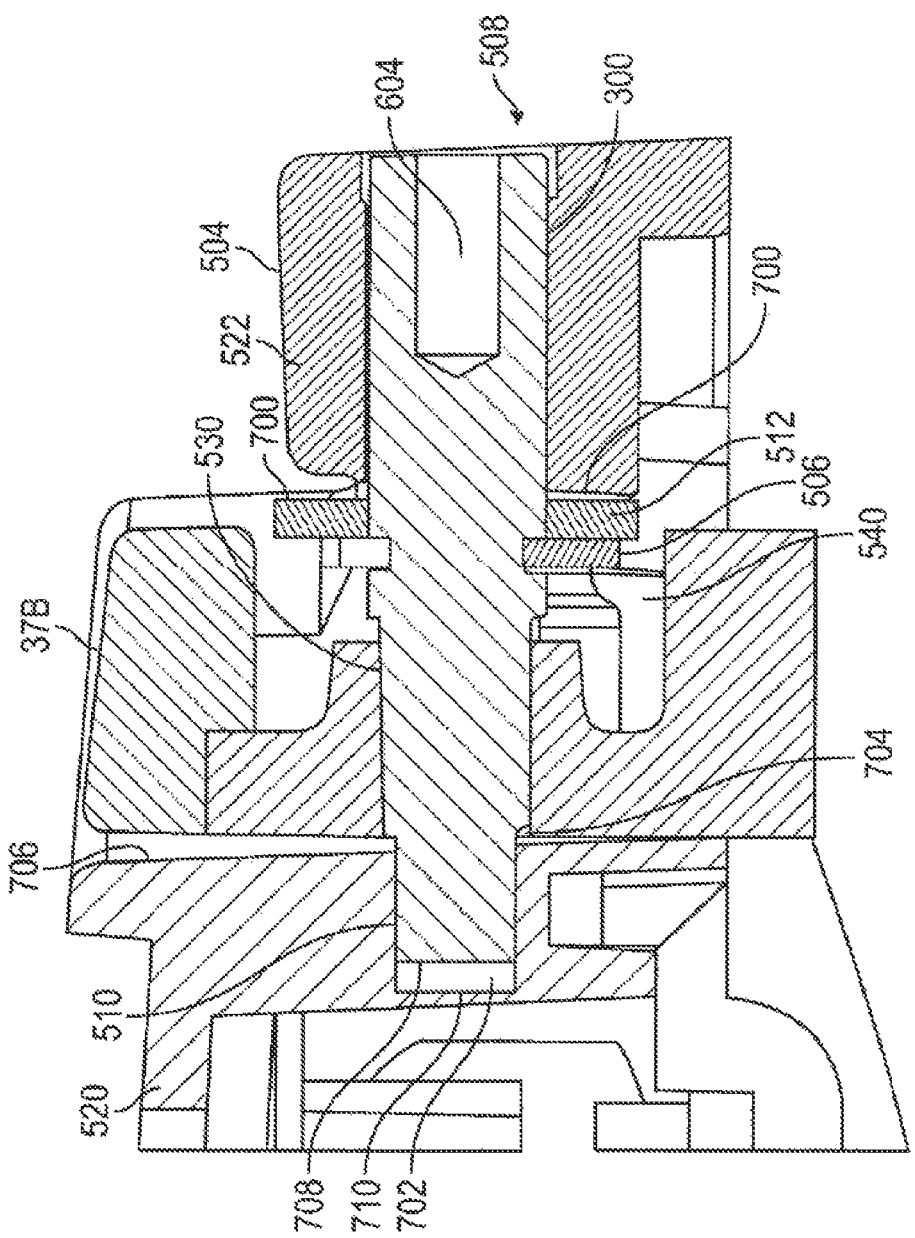
FIG. 7 illustrates a cross-sectional top view of an assembled latch assembly according to certain aspects of the present disclosure.

FIG. 7 is a cross-sectional top view of the latch assembly of door 30 in an assembled configuration, in accordance with an embodiment. In the example of FIG. 7, pin 300 extends through opening 508 in outer portion 522 of housing 504, through opening 530 in recess 540, and partially into opening 510 in inner portion 520 of housing 504. As shown in the example of FIG. 7, opening 510 may be a blind hole in inner portion 520. Also shown in FIG. 7 is washer 512 disposed between the door housing wall 700 and E-clip retainer 506 along tapered pivot latch pin 300. In this configuration, washer 512 prevents contact between door wall 700 and E-clip 506 and provides a smooth surface for E-clip 506 to oscillate against, thereby reducing or eliminating E-Clip stretch wear.

As shown in FIG. 7, pin 300 may be provided with a wear-relief feature such as wear-relief chamfer 704 that prevents pin 300 from coming into contact with the inner wall 706 of housing 504 if, over time, pin creep is present. For example, in configurations in which pin 300 is a hardened steel pin and hook portion 500 is formed from a relatively softer molded sintered steel, pin creep may arise when the hardened steel tapered pin is pushed into the relatively softer sintered steel hook, during "chucking", thereby deforming the hook's tapered hole 530. However, the tapered interface formed by tapered portion 600 and the inner surface of tapered hole 530 may provide a self-compensating chucking device that self-compensates for pin creep by allowing pin 300 to move deeper into hole 530 such that a wider portion of the tapered surface of pin 300 engages the deformed hole 530 to provide the same binding friction.

As shown in FIG. 7, an air gap 702 may be provided between the inner end 708 of pin 300 and the bottom 710 of opening 510 that allows pin 300 to move deeper into openings 530 and 510 without the pin bottoming out in opening 510. As shown, the tapered portion of the tapered pin 300 is partially disposed in the opening 530 in the recess 540 of the handle 37b and extends from the opening 530 in the recess 540 of the handle 37b into the recess 540 so that the tapered portion 600 can move further into opening 530 in the presence of pin creep.

Wear-relief chamfer 704 may, for example, be a 10-15 mil chamfer that can accommodate, for example, 3-5 mils of wear over the lifetime of assembly 650. As shown in FIG. 7, wear-relief chamfer 704 may be disposed adjacent an inner edge of the opening 530 in the recess 540 of the handle 37b.

The tapered interface between pin 300 and opening 530 may thus establish a stable, self-centering, self-compensating, axial alignment between the chucking assembly's mating components thereby allowing smooth repeatable motion of door handle 37b over repeated opening and closing of door 30.

Figure 8:
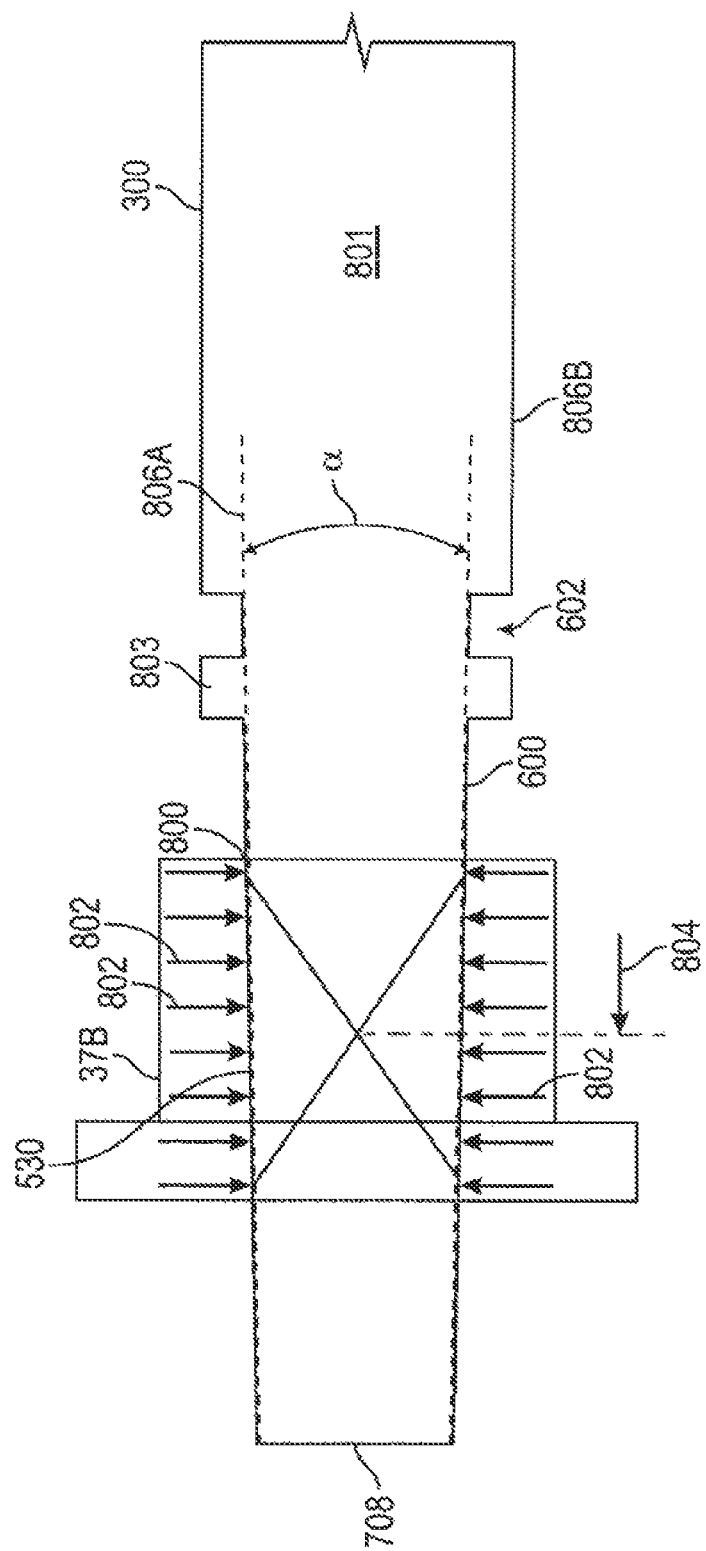
FIG. 8 illustrates a cross-sectional view of a tapered pin for a latch assembly according to certain aspects of the present disclosure.

FIG. 8 is an enlarged view of a portion of pin 300 engaged in opening 530 in hook portion 500. Other portions of door assembly 30 are omitted from FIG. 8 to facilitate viewing of tapered interface 800 formed from the outer surface of tapered portion 600 of pin 300 and the inner surface of opening 530. As shown by dashed lines 806A and 806B, tapered interface 800 may define a taper of angle $\alpha$. Angle $\alpha$ may, for example, be a two-degree angle, an angle of less than two degrees (e.g., a one-degree angle, a 1.5 degree angle, or a 1.8 degree angle), or an angle of more than two degrees (e.g., a 2.5 degree angle, a three degree angle, a four degree angle, or a five degree angle).

As shown in FIG. 8, groove 602 may be formed between a cylindrical outer portion 801 of pin 300 and an annular extension 803 of pin 300. Annular extension 803 may be disposed between groove 602 and tapered portion 600 of pin 300.

Contact at the interface 800 along a length of tapered portion 600 may also prevent or limit lateral play of pin 300 within opening 530 so that a perpendicular bisector (e.g., as indicated by arrow 804) of the outer surface of portion 600 that passes through the axis of pin 300 is not displaced, even in the presence of forces on pin 300 that would otherwise cause non-axial rotation of pin 300 within opening 530.

The frictional binding load generated by the chucking tapered interface 800 (as indicated, for example, by arrows 802) may provide the advantages over conventional systems of eliminating the need for a thread-lock adhesive and providing a tapered interface that breaks away easily when the assembly is relaxed and in a non-chucking state allowing the assembly to be separable and thereby enabling reuse of components (as examples).

Figure 9:
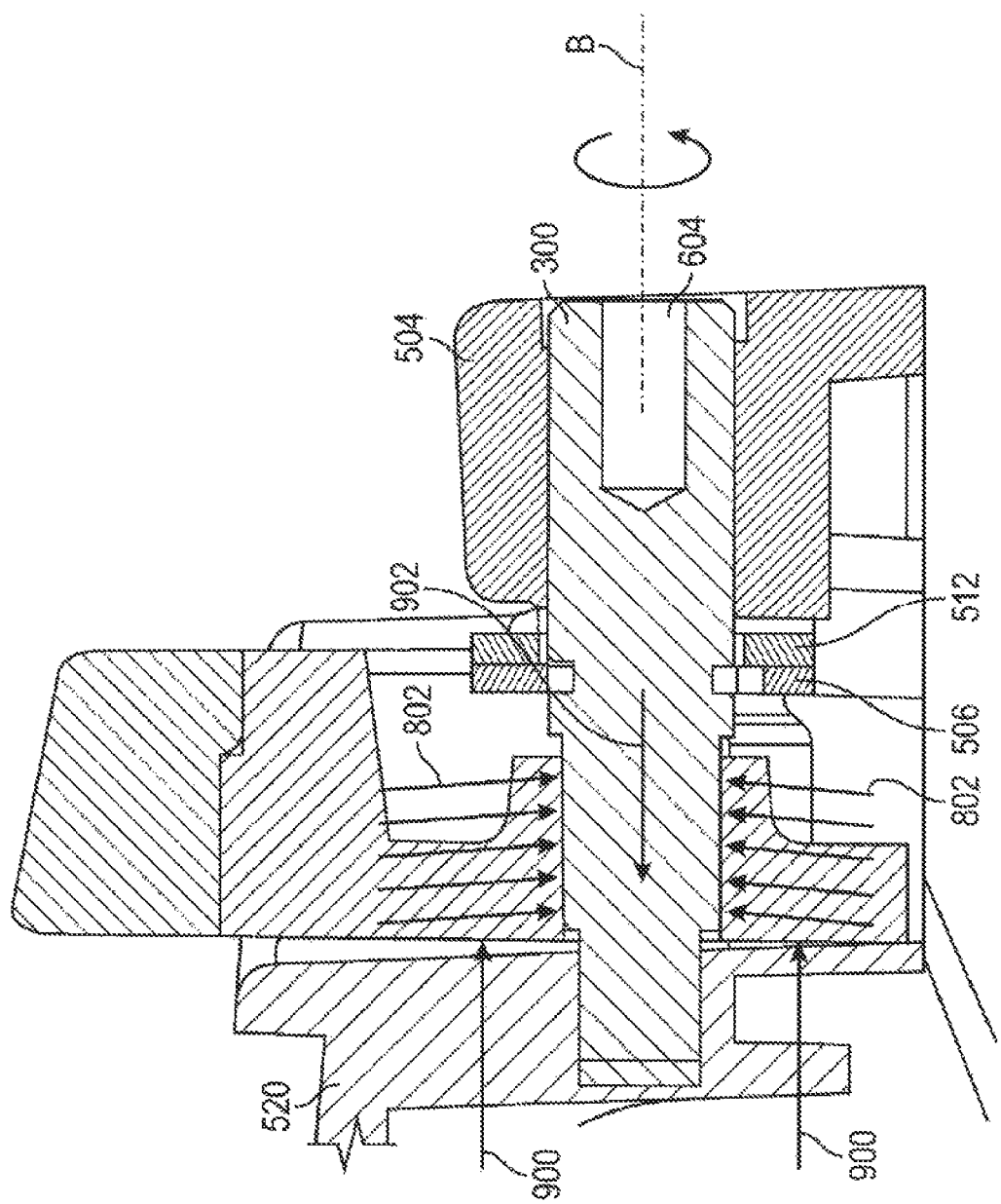
FIG. 9 illustrates a cross-sectional top view of an assembled latch assembly showing various exemplary load forces on the assembly during operation according to certain aspects of the present disclosure.

FIG. 9 is a cross-sectional top view of the latch assembly of door 30 in an assembled configuration and showing various load forces on the assembly, in accordance with an embodiment. The example of FIG. 9 is a free body diagram showing how the "chucking" effect is generated. The cross-section of FIG. 9 shows a cross-section of the portion of pump module 20 referenced by the dashed circle 459 shown in FIG. 4A.

As shown in FIG. 9, a handle closure load 900 may be generated on handle 37b during closing that pushes outwardly on the handle. However, pin 300, in cooperation with e-clip 506, provide a pin counter force 902 in opposition to the load 900, thus generating the tapered interface chucking force indicated by arrows 802. In this way, the tapered pin and the tapered opening are configured such that a door closing force on the door that is sufficient to overcome resistance from internal components of the IV pump that capture the IV tubing and sufficient to place the cam surface in alignment with the corresponding cam feature generates a lateral force along the tapered pin and tapered opening that pushes an outer tapered surface of the tapered pin into and along a tapered inner surface of the tapered opening causing chucking or binding.

The tapered pin and the tapered opening can thus be configured to continuously slide along a tapered inclined interface to compensate for wear and maintain a binding or chucking condition that absorbs slackness or looseness resulting from a gradual wear of the tapered opening by contact with the tapered pin.

Extraction hole 604 may provide for ease of disassembly during door maintenance and may provide a unique identity feature for pin 300. Moreover, a tapered interface configuration as described herein is difficult to counterfeit as the mating component's taper geometry is tightly controlled during the machining processes. As such, deviations from the specified tolerances between tapered mating parts will prevent proper component interaction and mechanism function.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. An infusion pump, comprising:
  a housing;
  at least one pumping mechanism; and
  a pivoting door configured to close and latch to secure infusion tubing to the at least one pumping mechanism, wherein the pivoting door comprises:
    a handle having recess and an opening in the recess;
    a door housing having an inner portion and an outer portion; and
    a tapered pin that extends through an opening in the outer portion, a co-aligned opening in the recess of the handle, and a co-aligned opening in the inner portion.

Concept 2. The infusion pump of Concept 1 or any other Concept, wherein the opening in the recess of the handle comprises a tapered opening having a tapered inner surface with a taper that corresponds to a taper of the tapered pin.

Concept 3. The infusion pump of Concept 2 or any other Concept, wherein the tapered pin comprises a tapered portion and a cylindrical portion and wherein the cylindrical portion is disposed within the opening in the outer portion of the door housing.

Concept 4. The infusion pump of Concept 3 or any other Concept, wherein the tapered portion of the tapered pin is partially disposed in the opening in the recess of the handle and extends from the opening in the recess of the handle into the recess.

Concept 5. The infusion pump of Concept 4 or any other Concept, wherein the tapered pin further comprises a groove disposed between the cylindrical portion and the tapered portion.

Concept 6. The infusion pump of Concept 5 or any other Concept, further comprising an E-clip retainer engaged in the groove that provides a mechanical stop that prevents the tapered pin from backing out of door housing.

Concept 7. The infusion pump of Concept 6 or any other Concept, wherein the tapered pin comprises a wear-relief chamfer adjacent an edge of the opening in the recess of the handle.

Concept 8. The infusion pump of Concept 7 or any other Concept, further comprising an air gap between an end of the tapered pin and a bottom of the opening in the inner portion of the door housing.

Concept 9. The infusion pump of Concept 8 or any other Concept, further comprising a washer disposed between the E-clip retainer and an inner wall of the outer portion of the housing.

Concept 10. The infusion pump of Concept 1 or any other Concept, wherein the tapered pin comprises a tapered portion having a taper of approximately two degrees.

Concept 11. The infusion pump of Concept 10 or any other Concept, wherein the opening in the recess of the handle comprises a corresponding taper of approximately two degrees.

Concept 12. The infusion pump of Concept 1 or any other Concept, wherein the handle comprises a sintered steel handle and wherein the tapered pin comprises a relatively harder hardened steel pin.

Concept 13. The infusion pump of Concept 12 or any other Concept, wherein the handle comprises a hook portion, wherein the recess is disposed in the hook portion, and wherein the hook portion comprises a cam surface.

Concept 14. The infusion pump of Concept 13 or any other Concept, further comprising a boss disposed on the housing, the boss configured to engage with the cam surface of the hook portion of the handle to press the tapered pin into the opening in the recess in the hook portion when the cam surface is pressed against the boss by a closing force on the handle.

Concept 15. The infusion pump of Concept 1 or any other Concept, further comprising a threaded extraction hole in the tapered pin.

Concept 16. A latching door handle assembly for a door of an infusion pump, comprising:
 a molded handle having a hook portion with a recess and a tapered opening in the recess; and
 a tapered pin, wherein the tapered pin comprises:
  a tapered portion configured to engage in the tapered opening; and
  a groove configured to receive an E-clip disposed in the recess.

Concept 17. The latching door handle assembly of Concept 16 or any other Concept, further comprising a cam surface on the hook portion, wherein the cam surface is configured to transfer a force on the cam surface into a force that presses the tapered pin into the tapered opening.

Concept 18. The latching door handle assembly of Concept 16 or any other Concept, further comprising:
 a torsion spring that extends around the tapered opening in the recess; and
 a washer on the tapered pin; and
 the E-clip disposed in the groove between the torsion spring and the washer.

Concept 19. A fluid infusion system, comprising:
 an intravenous (IV) set having IV tubing; and
 an IV pump having a pumping module and a door, wherein a pumping segment of the IV tubing is secured to the pumping module by the door, and wherein the door comprises:
  a door housing having an outer portion, an inner portion, and an air gap between the outer portion and the inner portion;
  a handle having a tapered opening disposed in the air gap; and
  a latching door handle assembly that includes a tapered pin that extends through an opening in the outer portion, through the tapered opening in the air gap, and into a co-aligned opening in the inner portion.

Concept 20. The fluid infusion system of Concept 19 or any other Concept, wherein the latching door handle assembly further comprises:
 a hook portion having a cam surface configured to engage a corresponding cam feature on the pumping module;
 an E-clip retainer engaged with a recess on the tapered pin;
 a washer disposed between the E-clip retainer and the outer portion of the door housing; and
 a torsion spring disposed between the E-clip retainer and a portion of the handle.

Concept 21. The fluid infusion system of Concept 20 or any other Concept, wherein the tapered pin and the tapered opening are configured such that a door closing force on the door that is sufficient to overcome resistance from internal components of the IV pump that capture the IV tubing and to place the cam surface in alignment with the corresponding cam feature generates a lateral force along the tapered pin and tapered opening that pushes an outer tapered surface of the tapered pin into and along a tapered inner surface of the tapered opening causing chucking or binding.

Concept 22. The fluid infusion system of Concept 21 or any other Concept, wherein the tapered pin and the tapered opening are configured to continuously slide along a tapered inclined interface to compensate for wear and maintain a binding or chucking condition that absorbs slackness or looseness resulting from a gradual wear of the tapered opening by contact with the tapered pin.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A latching door handle assembly for a door of an infusion pump, comprising:
    a molded handle having a hook portion with a recess and a tapered opening in the recess; and
    a tapered pin, wherein the tapered pin comprises:
        a progressively tapered portion configured to engage in the tapered opening, wherein the tapered portion comprises a tapered portion angle of approximately two degrees relative to a longitudinal axis of the tapered pin, wherein the tapered portion angle is configured to generate a chucking force along a tapered inner surface of the tapered opening to permit the tapered pin and the molded handle to rotate together; and
        a groove configured to receive an E-clip disposed in the recess.

2. The latching door handle assembly of claim 1, wherein the tapered opening comprises the tapered inner surface with a taper that corresponds to the tapered portion angle of the tapered pin.

3. The latching door handle assembly of claim 2, wherein the tapered pin comprises a cylindrical portion.

4. The latching door handle assembly of claim 3, wherein the tapered portion of the tapered pin is partially disposed in the tapered opening in the recess of the molded handle and extends from the tapered opening in the recess of the molded handle into the recess.

5. The latching door handle assembly of claim 1, wherein the molded handle comprises a sintered steel handle and wherein the tapered pin comprises a hardened steel pin which is relatively harder than the sintered steel handle.

6. The latching door handle assembly of claim 1, further comprising a cam surface on the hook portion, wherein the cam surface is configured to transfer a force on the cam surface into a force that presses the tapered pin into the tapered opening.

7. The latching door handle assembly of claim 6, further comprising a boss disposed on the infusion pump, the boss configured to engage with the cam surface of the hook portion of the molded handle to press the tapered pin into the tapered opening in the recess in the hook portion when the cam surface is pressed against the boss by a closing force on the molded handle.

8. The latching door handle assembly of claim 1, further comprising:
    a torsion spring that extends around the tapered opening in the recess; and
    a washer on the tapered pin; and
    the E-clip disposed in the groove between the torsion spring and the washer.

9. The latching door handle assembly of claim 8, wherein the washer is disposed between the E-clip and an inner wall of an outer portion of the infusion pump.

10. The latching door handle assembly of claim 1, wherein the tapered opening has a tapered opening angle of approximately 2 degrees, and the tapered portion angle and the tapered opening angle are configured to generate the chucking force along the tapered inner surface.

11. The latching door handle assembly of claim 1, wherein the progressively tapered portion comprises a continuously inclined surface.

12. A fluid infusion system, comprising:
    an intravenous (IV) set having IV tubing; and
    an IV pump having a pumping module and a door, wherein a pumping segment of the IV tubing is secured to the pumping module by the door, and wherein the door comprises:
        a door housing having an outer portion, an inner portion, and an air gap between the outer portion and the inner portion;
        a handle having a tapered opening disposed in the air gap; and
        a latching door handle assembly that includes a tapered pin that extends through an opening in the outer portion, through the tapered opening in the air gap, and into a co-aligned opening in the inner portion, wherein the tapered pin comprises a progressively tapered portion having a tapered portion angle of approximately two degrees relative to a longitudinal axis of the tapered pin, wherein the tapered portion angle is configured to generate a chucking force along a tapered inner surface of the tapered opening to permit the tapered pin and the handle to rotate together.

13. The fluid infusion system of claim 12, wherein the latching door handle assembly further comprises:
a hook portion having a cam surface configured to engage a corresponding cam feature on the pumping module;
an E-clip retainer engaged with a recess on the tapered pin;
a washer disposed between the E-clip retainer and the outer portion of the door housing; and
a torsion spring disposed between the E-clip retainer and a portion of the handle.

14. The fluid infusion system of claim 13, wherein the tapered pin and the tapered opening are configured such that a door closing force on the door that is sufficient to overcome resistance from internal components of the IV pump that capture the IV tubing and to place the cam surface in alignment with the corresponding cam feature generates a lateral force along the tapered pin and the tapered opening that pushes an outer tapered surface of the tapered pin into and along the tapered inner surface of the tapered opening causing chucking or binding.

15. The fluid infusion system of claim 14, wherein the tapered pin is configured to continuously slide along a tapered inclined interface of the tapered opening to compensate for wear and maintain a binding or chucking condition that absorbs slackness or looseness resulting from a gradual wear of the tapered opening by contact with the tapered pin.

16. The fluid infusion system of claim 13, wherein the E-clip retainer provides a pin counterforce to generate the chucking force.

17. The fluid infusion system of claim 13, wherein the tapered opening comprises the tapered inner surface with a taper that corresponds to the tapered portion angle of the tapered pin.

18. The fluid infusion system of claim 13, wherein the tapered pin comprises the tapered portion and a cylindrical portion and wherein the cylindrical portion is disposed within the opening in the outer portion of the door housing.

19. The fluid infusion system of claim 18, wherein the tapered portion of the tapered pin is partially disposed in the tapered opening of the handle and extends from the tapered opening of the handle through the tapered opening.

20. The fluid infusion system of claim 12, further comprising a threaded extraction hole in the tapered pin.

* * * * *